(12) United States Patent
Melnyk et al.

(10) Patent No.: US 12,299,849 B2
(45) Date of Patent: May 13, 2025

(54) NOISE PRESERVING MODELS AND METHODS FOR RESOLUTION RECOVERY OF X-RAY COMPUTED TOMOGRAPHY IMAGES

(71) Applicants: GE Precision Healthcare LLC, Wauwatosa, WI (US); Purdue Research Foundation, West Lafayette, IN (US); University of Notre Dame du Lac, South Bend, IN (US)

(72) Inventors: Roman Melnyk, New Berlin, WI (US); Madhuri Mahendra Nagare, Karmala (IN); Jie Tang, Merion Station, PA (US); Obaidullah Rahman, South Bend, IN (US); Brian E Nett, Wauwatosa, WI (US); Ken Sauer, South Bend, IN (US); Charles Addison Bouman, Jr., West Lafayette, IN (US)

(73) Assignees: GE Precision Healthcare LLC, Waukesha, WI (US); Purdue Research Foundation, West Lafayette, IN (US); University of Notre Dame du Lac, South Bend, IN (US)

( * ) Notice: Subject to any disclaimer, the term of this patent is extended or adjusted under 35 U.S.C. 154(b) by 406 days.

(21) Appl. No.: 17/807,779

(22) Filed: Jun. 20, 2022

(65) Prior Publication Data
US 2023/0410259 A1    Dec. 21, 2023

(51) Int. Cl.
*G06T 5/70* (2024.01)
*A61B 6/03* (2006.01)
*G06T 7/00* (2017.01)

(52) U.S. Cl.
CPC ............... *G06T 5/70* (2024.01); *A61B 6/032* (2013.01); *G06T 7/0012* (2013.01); *G06T 2207/10081* (2013.01)

(58) Field of Classification Search
None
See application file for complete search history.

(56) References Cited

U.S. PATENT DOCUMENTS

| | | | | |
|---|---|---|---|---|
| 2011/0268328 A1* | 11/2011 | Bar-Aviv | | G06T 5/70 |
| | | | | 382/128 |
| 2012/0219215 A1* | 8/2012 | Lukac | | G06T 5/70 |
| | | | | 382/199 |

(Continued)

OTHER PUBLICATIONS

Tyler et al., "Beyond Fourth-order Texture Discrimination: Generation of Extreme-order and Statistically-balanced Textures", Vision Research, vol. 44, 18, 2004, pp. 2187-2199.

(Continued)

*Primary Examiner* — Delomia L Gilliard
(74) *Attorney, Agent, or Firm* — Amin, Turocy & Watson, LLP

(57) ABSTRACT

Noise preserving models and methods for resolution recovery of x-ray computed tomography (e.g., using a computerized tool) are enabled. For example, a system can comprise: a memory that stores computer executable components, and a processor that executes the computer executable components stored in the memory, wherein the computer executable components comprise: a pair generation component that generates a pair of images, the pair of images comprising an input image and a ground truth image, a training component that trains a machine learning based sharpening algorithm by approximately minimizing a loss function that determines an error between a sharpened image and the ground truth image, and a sharpening component that, using the sharpening algorithm, sharpens the input image to generate the sharpened image, wherein the sharpened image comprises a second noise that is similar in intensity to a first noise of the input image.

20 Claims, 11 Drawing Sheets

(56) References Cited

U.S. PATENT DOCUMENTS

| | | | |
|---|---|---|---|
| 2013/0202177 A1* | 8/2013 | Bar-Aviv | G06T 19/20 |
| | | | 382/128 |
| 2020/0065940 A1* | 2/2020 | Tang | G06T 3/40 |
| 2020/0388014 A1* | 12/2020 | Hiasa | G06N 3/047 |
| 2021/0118099 A1* | 4/2021 | Kearney | A61B 6/5217 |
| 2022/0375038 A1 | 11/2022 | Nagare et al. | |
| 2024/0062342 A1* | 2/2024 | Jangid | G06T 5/73 |

OTHER PUBLICATIONS

Solomon et al., "Quantitative Comparison of Noise Texture Across Ct Scanners From Different Manufacturers", Medical Physics, vol. 39, No. 10, Oct. 2012, pp. 6048-6055.

Nagare et al., "Image Enhancement Using Texture Matching Generative Adversarial Networks", U.S. Appl. No. 18/475,609, filed Sep. 27, 2023, 71 pages.

Nagare et al., "A Bias-reducing Loss Function for CT Image Denoising", IEEE International Conference on Acoustics, Speech and Signal Processing (ICASSP), 2021, pp. 1175-1179.

Nagare et al., "A Noise Preserving Sharpening Filter for CT Image Enhancement", IEEE International Conference on Image Processing (ICIP), 2022, 4 pages.

Gibson, James J., "The Perception of Visual Surfaces", The American Journal of Psychology, vol. 63, No. 3, 367-384, Jul. 1950, 4 pages.

Jagadeesh et al., "Texture-like Representation of Objects In Human Visual Cortex", Proceedings of the National Academy of Sciences, vol. 119, No. 17, e2115302119, Apr. 19, 2022, 13 pages.

Waite et al., "Analysis of Perceptual Expertise in Radiology-current Knowledge and A New Perspective", Frontiers in Human Neuroscience, vol. 13, No. 213, Jun. 25, 2019, 21 pages.

Kulathilake et al., "A Review on Self-adaptation Approaches and Techniques in Medical Image Denoising Algorithms", Multimedia Tools and Applications, vol. 81, Issue 26, Aug. 4, 2022, 38 pages.

Buades et al., "A Non-local Algorithm for Image Denoising", IEEE Computer Society Conference on Computer Vision and Pattern Recognition, vol. 2, 2005, 6 pages.

Li et al., "Adaptive Nonlocal Means Filtering Based on Local Noise Level for CT Denoising", Medical Physics, vol. 41, No. 1, Dec. 31, 2013, 16 pages.

Dabov et al., "Image Denoising by Sparse 3dD Transform-domain Collaborative Filtering", IEEE Transactions on Image Processing, vol. 16, No. 8, Aug. 2007, 16 pages.

Beister et al., "Iterative Reconstruction Methods in X-ray CT", Physica Medica, vol. 28, Issue 2, 2012, pp. 94-108.

Kang et al., "A Deep Convolutional Neural Network Using Directional Wavelets for Lowdose X-ray CT Reconstruction", Medical Physics, vol. 44, No. 10, Oct. 2017, 16 pages.

Chen et al., "Low-Dose CT with a Residual Encoder-Decoder Convolutional Neural Network (RED-CNN)", IEEE Transactions on Medical Imaging, vol. 36, No. 12, Dec. 2017, 38 pages.

Yang et al., "Low-Dose CT Image Denoising Using a Generative Adversarial Network with Wasserstein Distance and Perceptual Loss", IEEE Transactions on Medical Imaging, vol. 37, No. 6, Jun. 2018, 10 pages.

Li et al., "SACNN: Self-Attention Convolutional Neural Network for Low-Dose CT Denoising with Self-Supervised Perceptual Loss Network", In IEEE Transactions on Medical Imaging, vol. 39, No. 7, Jul. 2020, 13 pages.

You et al., "CT Super-resolution GAN Constrained by the Identical, Residual, and Cycle Learning Ensemble (GAN-CIRCLE)", IEEE Transactions on Medical Imaging, vol. 39, No. 1, Jan. 2020, 14 pages.

Xian et al., "TextureGAN: Controlling Deep Image Synthesis with Texture Patches", In Proceedings of the IEEE Conference On Computer Vision And Pattern Recognition, 2018, pp. 8456-8465.

Starck et al., "Image Decomposition via the Combination of Sparse Representations and a Variational Approach", IEEE Transactions on Image Processing, vol. 14, No. 10, Oct. 2005, pp. 1570-1582.

Zeng et al., "Magnetic Resonance Image Denoising Algorithm Based on Cartoon, Texture, and Residual Parts", Computational and Mathematical Methods in Medicine, Apr. 1, 2020, vol. 2020, Article ID 1405647, 10 pages.

Chen et al., "Image Denoising Algorithm Based on Structure and Texture Part", International Conference on Computational Intelligence and Security (CIS), 2016, pp. 147-151.

Goodfellow et al., "Generative Adversarial Nets", In Advances in Neural Information Processing Systems, vol. 27, 2014, URL https://proceedings.neurips.cc/paper/2014/file/5ca3e9b122f61f8f06494c97b1afccf3-Paper.pdf, 9 pages.

Bromley et al., "Signature Verification Using a "Siamese" Time Delay Neural Network", International Journal of Pattern Recognition and Artificial Intelligence, vol. 7 (4), 1993, 8 pages.

Goodfellow et al., "Deep Learning", MIT Press, http://www.deeplearningbook.org., 2016, 9 pages.

Isola et al., "Image-to-image Translation with Conditional Adversarial Networks", In Proceedings of the IEEE Conference on Computer Vision and Pattern Recognition, 2017, pp. 1125-1134.

Hsieh et al., "A New Era of Image Reconstruction: Truefidelity", Technical White Paper on Deep Learning Image Reconstruction, GE Healthcare, 2019, 15 pages.

Hsieh, Jiang, "Computed Tomography: Principles, Design, Artifacts, and Recent Advances", Spie Press, 3rd Edition, 2015, 17 pages.

Ghalati et al., "Texture Analysis and Its Applications in Biomedical Imaging: A Survey", IEEE Reviews in Biomedical Engineering, vol. 15, Dec. 7, 2022, pp. 222-246.

Melnyk et al., U.S. Appl. No. 17/807,779 titled "Noise Preserving Models and Methods for Resolution Recovery of X-ray Computed Tomography Images", filed on Jun. 20, 2022, 30 pages.

Cohen et al., "Distribution Matching Losses Can Hallucinate Features in Medical Image Translation", arXiv:1805.08841v3 [cs.CV] Oct. 3, 2018, 11 pages.

Arjovsky et al., "Wasserstein Generative Adversarial Networks", Proceedings of the 34th International Conference on Machine Learning, vol. 70, 2017, 10 pages.

Wang et al., "Image Quality Assessment: From Error Visibility to Structural Similarity", IEEE Transactions on Image Processing, vol. 13, No. 4, Apr. 2004, 14 pages.

Szczykutowicz et al., "A Review of Deep Learning CT Reconstruction: Concepts, Limitations, and Promise in Clinical Practice", Current Radiology Reports, vol. 10, No. 9, 2022, pp. 101-115.

Li, B. et al | "Resolution and noise trade-off analysis for volumetric CT". Medical physics, 34(10), Oct. 2007, pp. 3732-3738, 7 pages.

Jiang, M. et al. | "Blind deblurring of spiral CT images". IEEE Transactions on Medical Imaging, vol. 22, No. 7, Jul. 2003, pp. 837-845, 9 pages.

Thibault, J.B., et al. | A three-dimensional statistical approach to improved image quality for multislice helical CT. Medical physics, 34(11), 2007, pp. 4526-4544, 20 pages.

Zhang, R., Tet al. | "Model-based iterative reconstruction for dual-energy X-ray CT using a joint quadratic likelihood model". IEEE transactions on medical imaging, 33(1), 203, pp. 117-134, 18 pages.

Kuntz, J. et al. | "Focal spot deconvolution using convolutional neural networks". Proc. SPIE 10948, Medical Imaging 2019: Physics of Medical Imaging, 109480Q (Mar. 1, 2019); doi: 10.1117/12.2513400, 7 pages.

Yim, D. et al. | "A deep convolutional neural network for simultaneous denoising and deblurring in computed tomography". Journal of Instrumentation, 15(12), p. P12001, 12 pages.

Dong, C., et al. | "Image super-resolution using deep convolutional networks". IEEE transactions on pattern analysis and machine intelligence, arXiv:1501.00092v3 [cs.CV] Jul. 31, 2015, 14 pages.

Chen, M., Cet sil | "Learning Blind Denoising Network for Noisy Image Deblurring". In ICASSP 2020-2020 IEEE International Conference on Acoustics, Speech and Signal Processing, (ICASSP), May 2020, 5 pages.

Zhang, K., et al. | "Learning a single convolutional super-resolution network for multiple degradations". In Proceedings of the IEEE Conference on Computer Vision and Pattern Recognition, arXiv:1712.06116v2 [cs.CV] May 24, 2018, 10 pages.

(56) References Cited

OTHER PUBLICATIONS

Chi, J., Zet al. | Computed tomography (CT) image quality enhancement via a uniform framework integrating noise estimation and super-resolution networks. Sensors 2019, 19, 3348; doi:10.3390/s19153348, Published: Jul. 30, 2019, 20 pages.

Wolterink, J.M. et al. | "Generative adversarial networks for noise reduction in low-dose Ct". IEEE transactions on medical imaging, 36(12), Dec. 2017, pp. 2536-2545, 10 pages.

Dong, W., et al. | Image deblurring and super-resolution by adaptive sparse domain selection and adaptive regularization. IEEE Transactions on image processing, 20(7), 2011, 35 pages.

Zhang, K., et al. | Beyond a gaussian denoiser: Residual learning of deep cnn for image denoising. IEEE transactions on image processing, arXiv:1608.03981v1 [cs.CV] Aug. 13, 2016, 13 pages.

Phantom Laboratory, The | "Catphan 700 manual," Product guide, The Phantom Laboratory, 2021, 52 pages.

You, Ch. et al. | "Ct super-resolution gan constrained by the identical, residual, and cycle learning ensemble (gancircle)". asarXiv:1808.04256v3 [eess.IV] Sep. 6, 2018, 16 pages.

Kingma, P. et al. | "Adam: A method for stochastic optimization". arXiv:1412.6980v9 [cs.LG] Jan. 30, 2017, 15 pages.

Chollet, K. et al. | "Keras". Webpage https://keras.io, 2015, last accessed May 24, 2022, 5 pages.

* cited by examiner

| Resolution score | 0.7514 | 0.6369 |
|---|---|---|
| Noise std (HU) | 74.95 | 53.11 |

↖—202  ↖—204

| Resolution score | 0.6823 | 0.6811 |
|---|---|---|
| Noise std (HU) | 132.84 | 57.15 |

↖—206  ↖—208

NOISE PRESERVING MODELS AND METHODS FOR RESOLUTION RECOVERY OF X-RAY COMPUTED TOMOGRAPHY IMAGES

TECHNICAL FIELD

The disclosed subject matter relates to applications of machine learning in medical image processing and, more particularly, to noise preserving models and methods for resolution recovery of x-ray computed tomography images.

BACKGROUND

There is growing interest in the use of deep neural network (DNN) based image deblurring to enhance resolution of images. However, sharpening medical computed tomography (CT) images can be difficult, and can cause artifacts in the images. CT images can be noisy, for instance, because of a low x-ray dose constraint, and noise variance can increase along all dimensions, even with a linear reconstruction filter. Noise can further increase, for instance, for high-resolution kernels. Conventional methods for sharpening noiseless images tend to substantially amplify high-frequency noise in medical images. Hence, some conventional sharpening methods have attempted to employ some kind of denoising to suppress noise. Alternatively, DNN sharpening algorithms that are also designed to denoise tend to produce overly-smooth images that lack clinically important detail. Further, a combination of denoising and sharpening can produce an overly smooth result for clinical applications.

The above-described background relating to image sharpening is merely intended to provide a contextual overview of some current issues and is not intended to be exhaustive. Other contextual information may become further apparent upon review of the following detailed description.

DETAILED DESCRIPTION

Figure 1:
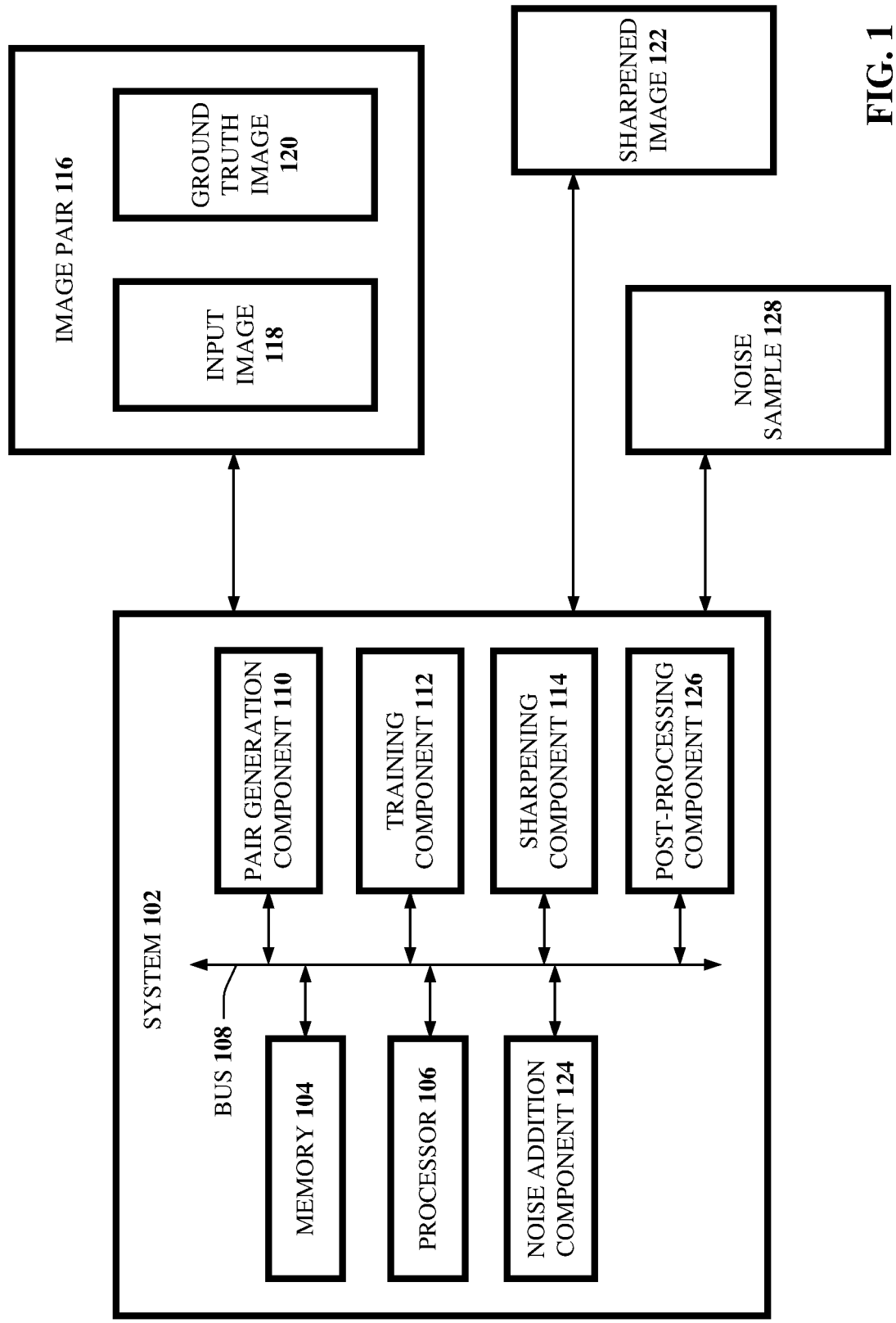
FIG. 1 is a block diagram of an exemplary system in accordance with one or more embodiments described herein.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

As alluded to above, image sharpening can be improved in various ways, and various embodiments are described herein to this end and/or other ends.

According to an embodiment, a system can include a memory that stores computer executable components, and a processor that executes the computer executable components stored in the memory. The computer executable components include a pair generation component that generates a pair of images, the pair of images comprising an input image and a ground truth image, a training component that trains a machine learning based sharpening algorithm by approximately minimizing a loss function that determines an error between a sharpened image and the ground truth image, and a sharpening component that, using the sharpening algorithm, sharpens the input image to generate the sharpened image. The sharpened image includes a second noise that is similar in intensity to a first noise of the input image In one or more embodiments, an extent of the sharpening of the input image can be determined by the sharpening component and using the sharpening algorithm, based on an adjustable sharpening parameter.

In various implementations, the computer executable components can further include a noise addition component that adds noise to the pair of images. In this regard, the noise can be respectively scaled for the sharpened image and the input image so that the second noise is similar in intensity to the first noise. In some embodiments, an input image scaling factor for the added noise, applicable to the input image, can be based on a first adjustable parameter. In further embodiments, a ground truth scaling factor for the added noise, applicable to the ground truth image, can be based on a second adjustable parameter. In some implementations, one or more scaling factors for the added noise can be determined, by the noise addition component, to maintain the second noise similar in intensity to the first noise. In some embodiments, the added noise can be determined, by the noise addition component, using a water phantom. In various implementations, the added noise can be determined, by the noise addition component, by subtracting averaged, high-resolution noise from individual, high-resolution noise.

In additional embodiments, the computer executable components can further include a post-processing component that reduces artifacts in the sharpened image based on a local edge magnitude of the sharpened image. In further embodiments, the post-processing component can reduce artifacts in the sharpened image based on Hounsfield Unit values of the sharpened image.

In another embodiment, a method can include generating, by a system comprising a processor, a pair of images. The pair of images includes an input image and a ground truth image. The method further includes training, by the system, a machine learning based sharpening algorithm by approximately minimizing a loss function that determines an error between a sharpened image and the ground truth image, and using the sharpening algorithm, sharpening, by the system, the input image to generate the sharpened image. The sharpened image comprises a second noise that is similar in intensity to a first noise of the input image.

In various embodiments, an extent of the sharpening of the input image may be determined, using the sharpening algorithm, based on an adjustable sharpening parameter.

In some embodiments, the above-method can further include adding, by the system, noise to the pair of images. In this regard, the noise can be respectively scaled for the sharpened image and the input image so that the second noise is similar in intensity to the first noise.

In various implementations, an input image scaling factor for the added noise, applicable to the input image, can be based on a first adjustable parameter, and a ground truth scaling factor for the added noise, applicable to the ground truth image, can be based on a second adjustable parameter.

According to yet another embodiment, a non-transitory machine-readable storage medium can include executable instructions that, when executed by a processor, facilitate performance of operations, including generating a pair of images, the pair of images includes an input image and a ground truth image, training a machine learning based sharpening algorithm by approximately minimizing a loss function that determines an error between the sharpened image and the ground truth image, using the sharpening algorithm, sharpening the input image to generate the sharpened image, wherein the sharpened image comprises a second noise that is similar in intensity to a first noise of the input image, and adding noise to the pair of images, wherein the noise is respectively scaled for the sharpened image and the input image so that the second noise is similar in intensity to the first noise.

In various embodiments, one or more scaling factors for the added noise can be determined to maintain the second noise similar in intensity to the first noise.

In some embodiments, the added noise can be determined using a water phantom.

In one or more embodiments, the added noise can be determined by subtracting averaged, high-resolution noise from individual, high-resolution noise.

In some embodiments, the above-operations can further include reducing one or more artifacts in the sharpened image based on a local edge magnitude of the sharpened image.

In additional embodiments, the above-operations can further include reducing one or more artifacts in the sharpened image based on Hounsfield Unit values of the sharpened image.

It should be appreciated that additional manifestations, configurations, implementations, protocols, etc. can be utilized in connection with the following components described herein or different/additional components as would be appreciated by one skilled in the art.

It is noted that radiologists tend to strongly prefer images comprising a consistent level of noise. So, it is highly desirable that any DNN-based sharpening algorithm not substantially change noise energy and/or texture. In this regard, various embodiments and/or systems herein can utilize a DNN-based noise preserving sharpening filter (NPSF) to sharpen images (e.g., CT images or other medical images or non-medical images) while preserving noise energy in the resulting image (e.g., sharpened image), so that noise energy in the resulting image is similar to the noise in a corresponding input image. Embodiments herein can utilize one or more adjustable parameters that can enable flexibility to achieve a suitable noise-resolution tradeoff. In this regard, embodiments herein can sharpen highly noisy images while producing fewer artifacts and more desired texture and detail.

Embodiments herein can achieve the foregoing, for instance, by introducing appropriately scaled noise to both input and ground truth images (e.g., while training). It is noted that aliasing artifacts and noise can be abundant in high-resolution kernel images, so embodiments herein can be tuned to achieve sharper images while suppressing such artifacts and noise.

It is additionally noted that embodiments herein (e.g., facilitating NPSF) can parameterize the training process. While embodiments herein can improve resolution while maintaining noise, one or more adjustable parameters herein can be set to perform resolution improvement and denoising with a single network. In various embodiments herein, NPSF adjustable parameters can be tuned to sharpen CT images without affecting noise energy or texture. Various embodiments herein (e.g., facilitating NPSF) can utilize adjustable parameters (e.g., three adjustable parameters) that provide flexibility to achieve the desired resolution-noise tradeoff. It is noted that such adjustable NPSF parameters herein can be tuned to sharpen CT images while suppressing aliasing artifacts and noise. This can be particularly useful for CT images reconstructed with a high resolution kernel. Embodiments herein can further utilize edge intensity-based blending, which can avoid overcorrection for soft tissue while sharpening high density areas (e.g., for bone).

To this and other various ends, the disclosed subject matter provides systems and methods that facilitate noise preservation in resolution recovery of x-ray CT images. While various embodiments herein are directed to CT imaging, one or more aspects of the disclosed subject matter may be extended to other medical images modalities. For example, the types of medical image data that may be processed and optimized using the disclosed techniques can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), magnetic resonance imaging (MRI) images, ultrasound (US) images, color flow doppler (CD) images, positron emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques. The medical imaging processing models disclosed herein can also be configured to process three-dimensional (3D) images.

Turning now to FIG. 1, there is illustrated an example, non-limiting system 102 in accordance with one or more embodiments herein. System 102 can comprise a computerized tool and/or a deep neural network (DNN), which can be configured to perform various operations relating to situational navigation. The system 102 can comprise one or more of a variety of components, such as memory 104, processor 106, bus 108, pair generation component 110, training component 112, sharpening component 114, noise addition component 124, and/or post-processing component 126. In various embodiments, one or more of the memory 104, processor 106, bus 108, pair generation component 110, training component 112, sharpening component 114, noise addition component 124, and/or post-processing component 126 can be communicatively or operably coupled (e.g., over a bus or wireless network) to one another to perform one or more functions of the system 102.

According to an embodiment, the pair generation component 110 can generate one or more pairs of images (e.g., image pair 116). In various embodiments, such an image pair 116 can comprise an input image 118 and a ground truth image 120. Such a pairing of the input image 118 and ground truth image 120 can be predefined or can be determined (e.g., via the pair generation component 110) using machine learning and/or a neural network as later discussed in greater detail. In various embodiments, the image pair 116, input image 118, ground truth image 120, noise sample 128, and/or sharpened image 122 can be stored in and/or accessed from one or more suitable image repositories.

In various embodiments, X can comprise a noise-free high-resolution image and Y can comprise an observed blurred and noisy image. In this regard, the system 102 can recover $\tilde{X}$ from Y, in which $\tilde{X}$ comprises a high-resolution image which possesses noise energy similar to Y, but with less blur. To accomplish the foregoing, the training component 112 can train a machine learning based sharpening algorithm herein, for instance, by approximately minimizing a loss function that determines an error between a sharpened image and the ground truth image. It is noted that in various embodiments, an extent of the sharpening of an input image herein (e.g., input image 118) can be determined (e.g., via the training component 112 or another suitable component herein) based on one or more adjustable parameters (e.g., sharpening parameters) (e.g., parameter ρ). In this regard, the training component 112 can train a sharpening algorithm (e.g., $f_\theta(\ )$) with parameters θ by minimizing the mean squared error (MSE) defined by:

$$MSE_{\tilde{X}} = \mathbb{E}\left[\|\tilde{X} - \hat{X}\|^2\right], \quad \text{Equation (1)}$$

in which $$\hat{X} = f_\theta(Y) \quad \text{Equation (2)}$$

is an estimate of $\tilde{X}$.

Various embodiments can be configured to train (e.g., via the training component 112) the NPSF $f_\theta(\ )$ to create suitable training pairs $(Y_k, \tilde{X}_k)$ for k=1, ..., K. In some embodiments, $\tilde{X}_k$ can comprise a noise free image (e.g., ground truth image 120), and $Y_k$ can be created by blurring $\tilde{X}_k$ (e.g., via the training component 112). However, the foregoing does not account for sensor noise in the measured image $Y_k$. In this case, the system 102 can be trained to perform pure sharpening (e.g., via the sharpening component 114) without denoising. Thus, the system 102 can tend to enhance the noise that can be present in Y. In other embodiments, $\tilde{X}_k$ can comprise a noise free image, and $Y_k$ can be created by blurring $\tilde{X}_k$ (e.g., via the training component 112, noise addition component 124, or another suitable component herein) and adding noise (e.g., via the noise addition component 124). In this case, the system 102 can be trained (e.g., via the training component 112 and/or noise addition component 124) to both sharpen and denoise $Y_k$. The foregoing can better account for sensor noise in an image (e.g., an input image 118 and/or ground truth image 120). However, the foregoing can result in deblurred images (e.g., sharpened image 122) with too much noise reduction. Thus, the resulting image, $\hat{X}$ (e.g., sharpened image 122), of Equation (2) can lack the texture and detail that is highly desirable to radiologists. Therefore, the pair generation component 110 can generate training pairs, $(Y_k, \tilde{X}_k)$, that account for both noise (e.g., in the image $Y_k$) and also result in an estimated $\hat{X}$ that preserves noise energy, texture, and/or fine detail. The generation of training pairs (e.g., via the pair generation component 110) that result in a noise-preserving sharpening filter (NPSF) can be accomplished as follows. First, the system 102 can generate (e.g., via the pair generation component 110):

$$Y = G(\rho) * X + \lambda_1 W \quad \text{Equation (3)}$$

In which G(ρ) is a Gaussian filter with standard deviation ρ, $\lambda_1$ is a parameter that controls the noise energy added to the blurred image, and W is an image containing a sample of noise (e.g., noise sample 128) with desirable texture and noise variance $\sigma_n^2$. In particular, the noise sample (e.g., noise sample 128) can be produced (e.g., via the noise addition component 124) using scans of a water phantom. It is noted that in various embodiments herein, any suitable low-pass filter with a point spread function of an appropriate dimension can be employed to blur X in addition to and/or instead of the Gaussian filter in Equation (3).

Similarly, embodiments herein can generate the target image $\tilde{X}$, for instance, by adding (e.g., via the noise addition component 124) a scaled version of the same noise sample to the noise-free high-resolution image $$\tilde{X} = X + \lambda_2 W, \quad \text{Equation (4)}$$

in which $\lambda_2$ is a parameter that determines the added noise energy. It is noted that the noise can be respectively scaled for the sharpened image (e.g., sharpened image 122) and the input image (e.g., input image 118) so that second noise (e.g., of the sharpened image 122) is similar in intensity (e.g., within a defined threshold) to first noise (e.g., of the input image 118). In this regard, one or more scaling factors for the added noise can be determined (e.g., by the noise addition component 124) to maintain the second noise similar in intensity (e.g., within a defined threshold) to the first noise.

Next, the system 102 can determine (e.g., via the training component 112) the values of various adjustable parameters herein. For $\lambda_1$, embodiments herein can utilize:

$$\lambda_1 = \alpha \sqrt{\frac{\text{Var}[Y]}{\sigma_n^2}} \quad \text{Equation (5)}$$

in which α is an adjustable parameter (e.g., a first adjustable parameter), Var[Y] is the noise variance in the image Y, and $\sigma_n^2$ is the noise variance in W. The parameter $\lambda_2$ can then be set as $$\lambda_2 = \beta \lambda_1 \quad \text{Equation (6)}$$

in which β∈ [0, 1] is an adjustable parameter (e.g., a second adjustable parameter).

In this regard, the system 102 can utilize one or more (e.g., three) adjustable parameters herein (e.g., ρ, α, and β). Further in this regard, and in various embodiments herein, the parameter ρ can be utilized to control (e.g., via the sharpening component 114) a defined or desired level of sharpening, with large values of ρ producing more sharpening. Further, the parameter α (e.g., a first adjustable parameter) can determine the amount of noise added to the training pairs, and thereby control an amount of aliasing artifacts in the results. It is noted that larger values of α can result in fewer artifacts, but with a tradeoff of somewhat less detail. Finally, the value of β (e.g., a second adjustable parameter) can be utilized to determine the amount of noise in the output image (e.g., sharpened image 122), with larger values of β resulting in more noise, but also more detail. In this regard, an input image scaling factor for the added noise, applicable to the input image, can be based on a first adjustable parameter (e.g., α) and/or a ground truth scaling factor for the added noise, applicable to the ground truth image, can be based on a second adjustable parameter (e.g., β). In particular, the value $\beta_{NPSF}$ can correspond to the parameter value so that $\sigma_{output}^2 = \sigma_{input}^2$ in which the output noise variance is matched to the input noise variance. In various embodiments, the value of $\beta_{NPSF}$ can be determined experimentally (e.g., via the training component 112), using machine learning herein, and/or otherwise determined.

For clinicians, images reconstructed with high resolution kernels can be highly useful for viewing high-density bones. In this regard, embodiments herein can improve the resolution of high-density bone structures, for instance, by utilizing a large value of ρ. However, a large ρ can sometimes overcorrect soft tissue boundaries. To avoid this overcorrection, one or more embodiments herein can perform edge magnitude-based blending (e.g., via the post-processing component 126) in which the result $\hat{X}$ of Equation (2) can be utilized in the bone regions of the reconstructions, and Y can be utilized in the soft tissue regions of the reconstruction. In this regard, the post-processing component 126 can reduce artifacts in the sharpened image based on a local edge magnitude of the sharpened image and/or based on Hounsfield Unit (HU) values of the sharpened image. To accomplish the foregoing, the post-processing component 126 can start by first computing the edge magnitude, E, from input Y as:

$$E = \|\nabla G(\rho_b) * Y\|, \quad \text{Equation (7)}$$

in which ∇ is a gradient operation and $G(\rho_b)$ is a Gaussian filter with standard deviation $\beta_b$. E can then be scaled linearly to the range of [0, 1] using the following transformation:

$$\tilde{E}_s = \frac{E_s - E_{min}}{E_{max} - E_{min}}, \quad \text{Equation (8)}$$

in which $E_s$ is the edge magnitude for the $s^{th}$ pixel, $E_{min}$ is the minimum edge magnitude and $E_{max}$ is the maximum edge magnitude to be considered for the linear scaling. In order to make the transformation robust to outliers, the post-processing component 126 can select $E_{min}$ and $E_{max}$ to be edge magnitudes at the $10^{th}$ percentile and the $90^{th}$ percentile of all the pixels, respectively, though it is noted that the foregoing is exemplary and other suitable percentiles can be utilized. Then the blended sharper image (e.g., sharpened image 122) can then be computed (e.g., via the post-processing component 126 and/or sharpening component 114) as:

$$\hat{X}_s^{(b)} = Y_s + (\hat{X}_s - Y_s)\tilde{E}_s. \quad \text{Equation (9)}$$

Because blending can be computed based on edge magnitude in the input image (e.g., input image 118) in which soft tissue boundaries comprise a lower edge magnitude, such blending herein (e.g., via the post-processing component 126 and/or the sharpening component 114) can avoid extreme sharpening and overcorrection in soft tissue.

Figure 2:
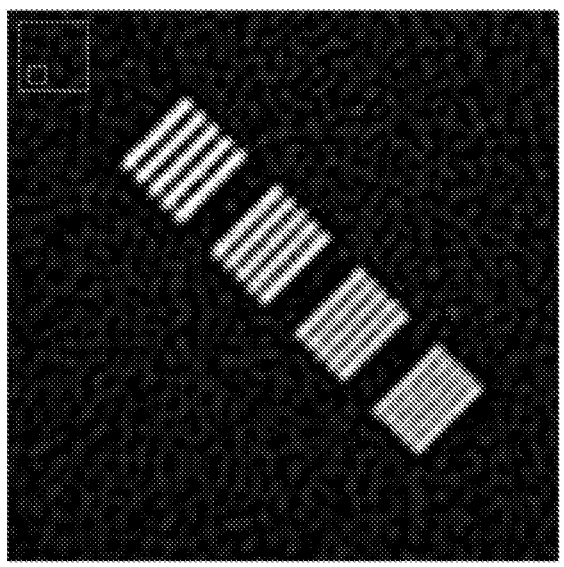
FIG. 2 illustrates various exemplary sharpening results in accordance with various embodiments described herein.
Figure 2:
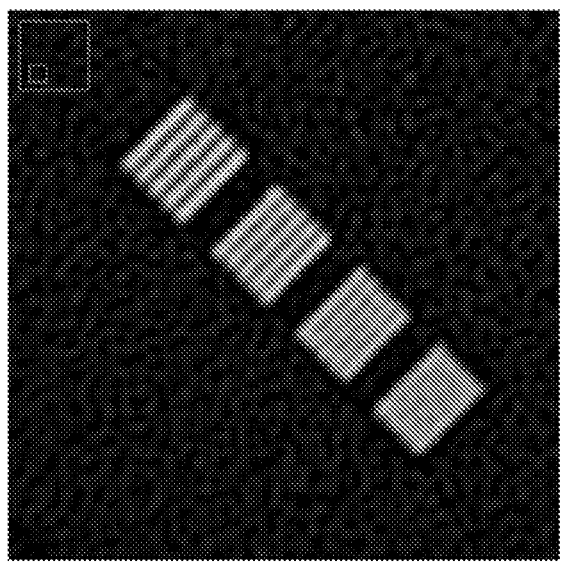
Figure 2:
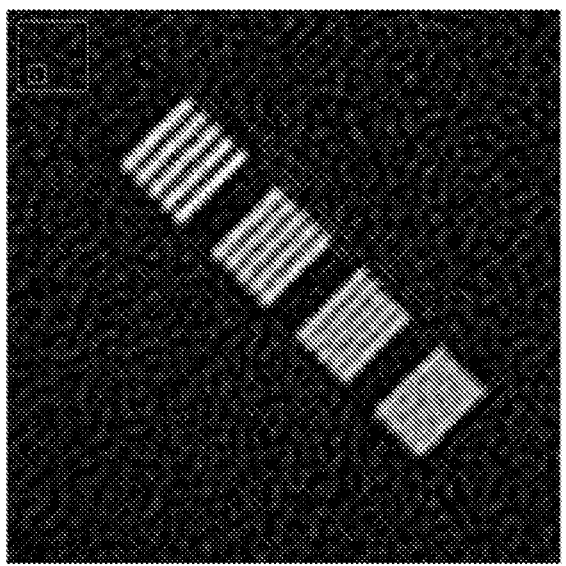
Figure 2:
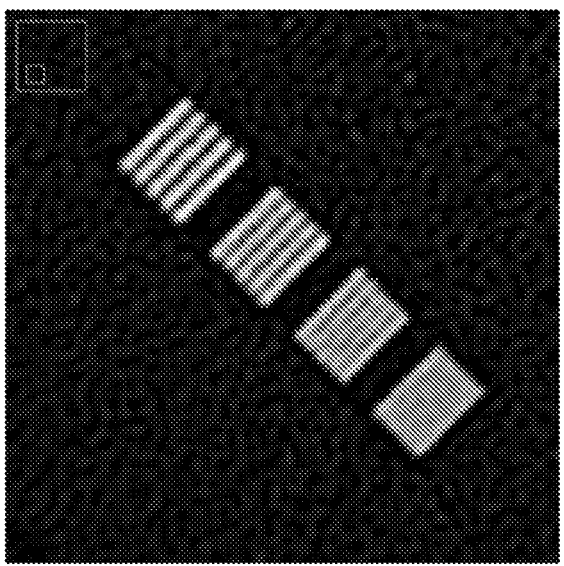

FIG. 2 demonstrates various exemplary results in accordance with various embodiments described herein (e.g., for a Bone+kernel). It is noted that results herein are shown for a Catphan 700 phantom, though other suitable phantoms can be utilized. The resolution section of the Catphan 700 phantom comprises line pairs arranged at various spatial frequencies. In this regard, image 202 and image 204 show ground truth and input line pairs scanned with a small and extra large (XL) focal spot, respectively. Image 208 illustrates a result image sharpening herein (e.g., via a system 102) as compared to conventional image sharpening in image 206. The resolution improvement (e.g., between image 204, image 208, and image 206) can be quantified with a score. A higher resolution score is indicative of sharper results. According to a non-limiting embodiment, the resolution score can be computed as follows:

--- total_Groups ← 4
peaks_in_Group ← 5
difficulty_for_Group[1 : total_Groups] ← 0
for k = 1 : total_Groups
  for j = 1 : peaks_in_Group-1

$$p'^{(k)}_j = \frac{p^{(k)}_j + p^{(k)}_{j+1}}{2}$$

difficulty_for_Group[k] ← difficulty_for_Group$[k] + \frac{p'^{(k)}_j}{v^{(k)}_j}$ end
  difficulty_weight$[k] \leftarrow \frac{1}{\text{difficulty\_for\_Group}[k]}$ end difficulty_weight $\leftarrow \frac{\text{difficulty\_weight}}{\sum_k \text{difficulty\_weight}[k]}$ resolution_score_Line1 ← 0
$D_{Al}$ ← 2300 HU
for k = 1 : total_Groups
  t ← 0
  for j = 1 : peaks_in_Group $$t \leftarrow t + \frac{D_{Al}}{p^{(k)}_{\hat{x}_j}}$$

end
  resolution_score_Line1 ← resolution_score_Line1 + t × difficulty_weight[k]
end Note:
$p_{\hat{x}_j}^{(k)}$: $j^{th}$ peak of $k^{th}$ line group along line 1 in an image $\hat{x}$
$p_j^{(k)}$: $j^{th}$ peak of $k^{th}$ line group along line 1 in the ground truth image
$v_j^{(k)}$: $j^{th}$ valley of $k^{th}$ line group along line 1 in the ground truth image
$D_{Al}$: HU number for the wire material in the Catphan phantom

---

Figure 3:
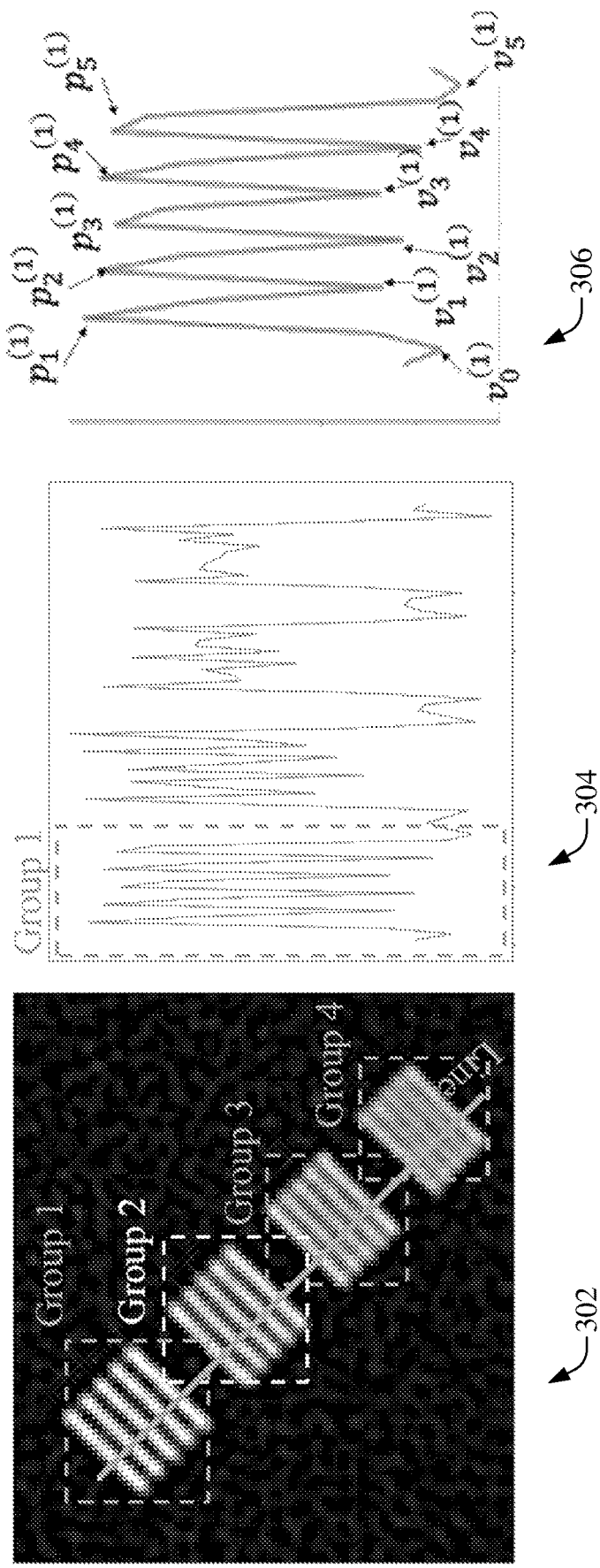
FIG. 3 illustrates an exemplary method to compute the resolution score to characterize various embodiments described herein.

To determine the resolution score for a result image $\hat{x}$ (e.g., via the system 102), line pairs can be processed in groups (e.g., group 1, group 2, group 3, group 4) as shown in FIG. 3, in which image 302 represents Catphan 700 phantom line pairs (e.g., ground truth), image 304 represents a profile plot for line 1, and image 306 represents a zoomed profile plot for group 1. To compute the final score, resolution scores can be averaged (e.g., via the system 102) for multiple lines parallel to the line 1.

As shown in image 206 and image 208, similar resolution scores are achieved. However, in image 206, noise is increased by a factor of approximately 2.5, while the noise level in image 208 is similar to the input. Further, image 206 comprises a blocky texture on the line pairs and surrounding areas, which can be perceived as an artifact.

Figure 4:
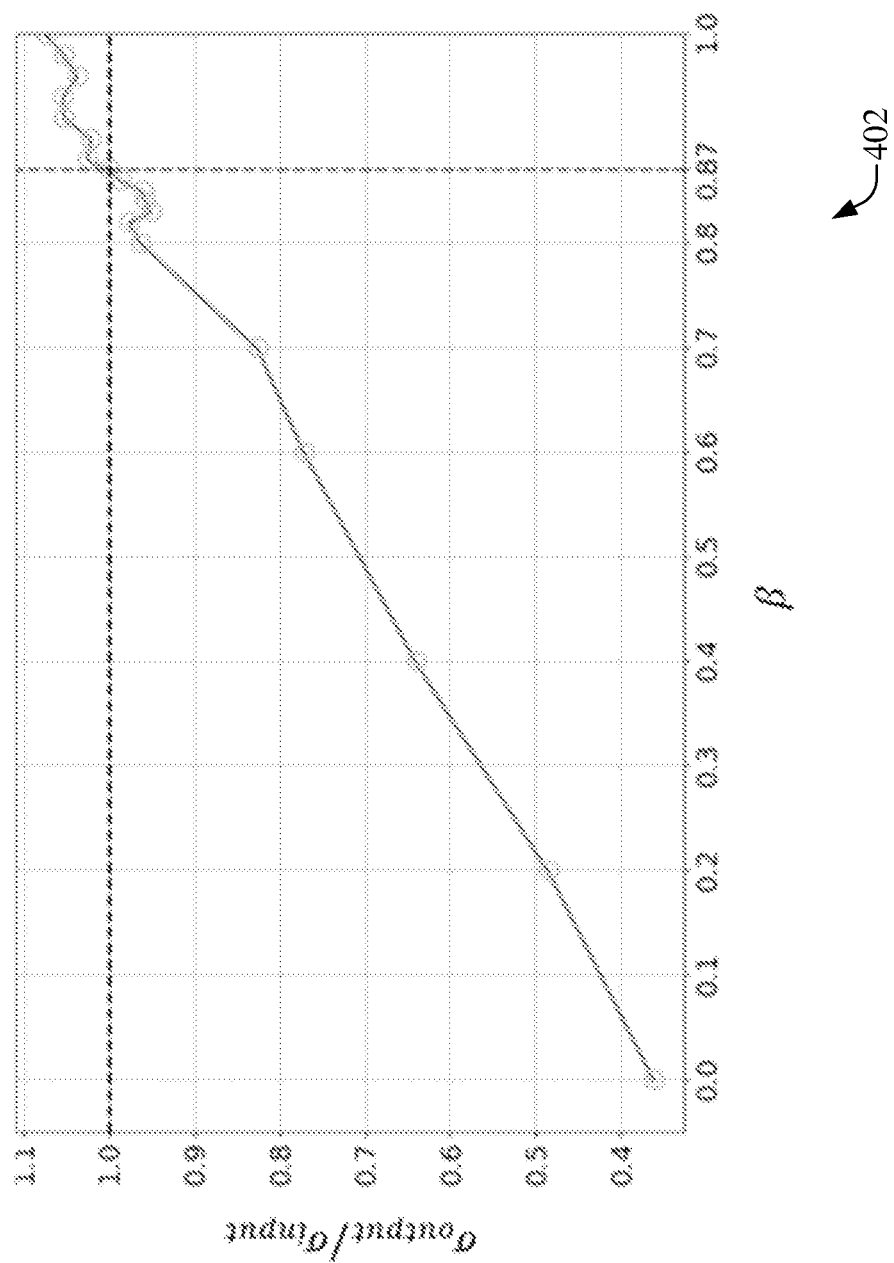
FIG. 4 illustrates an exemplary chart plotting $\sigma_{output}/\sigma_{input}$ for various values of $\beta$ in accordance with various embodiments described herein.

It is noted that the system 102 can sharpen clinical images for which a ground truth is not available. In this regard, to demonstrate the effect of β on the noise level in the NPSF results, FIG. 4 illustrates a chart 402, plotting $\sigma_{output}/\sigma_{input}$ for various values of β (e.g., when ρ is 0.7 and α is 1.0). Input noise variance $\sigma_{input}^2$ and noise variance of sharpened image $\sigma_{output}^2$ can be determined empirically (e.g., via the system 102 by computing the sample variance of uniform areas in various slices in a volume). In this regard, it can be determined (e.g., via the system 102) that maintaining β as 1 can result in higher noise in the results than in input. Therefore, in various embodiments herein, system 102 can set β to less than 1. In this example, for the setting {ρ=0.7, α=1.0}, $\beta_{NPSF}$ is 0.87. Additionally, FIG. 4 demonstrates that the parameter β (e.g., the second adjustable parameter herein) can be tuned to determine (e.g., via the system 102) a desired noise-resolution trade-off in the results (e.g., according to a defined criterion and/or using machine learning herein).

Figure 5:
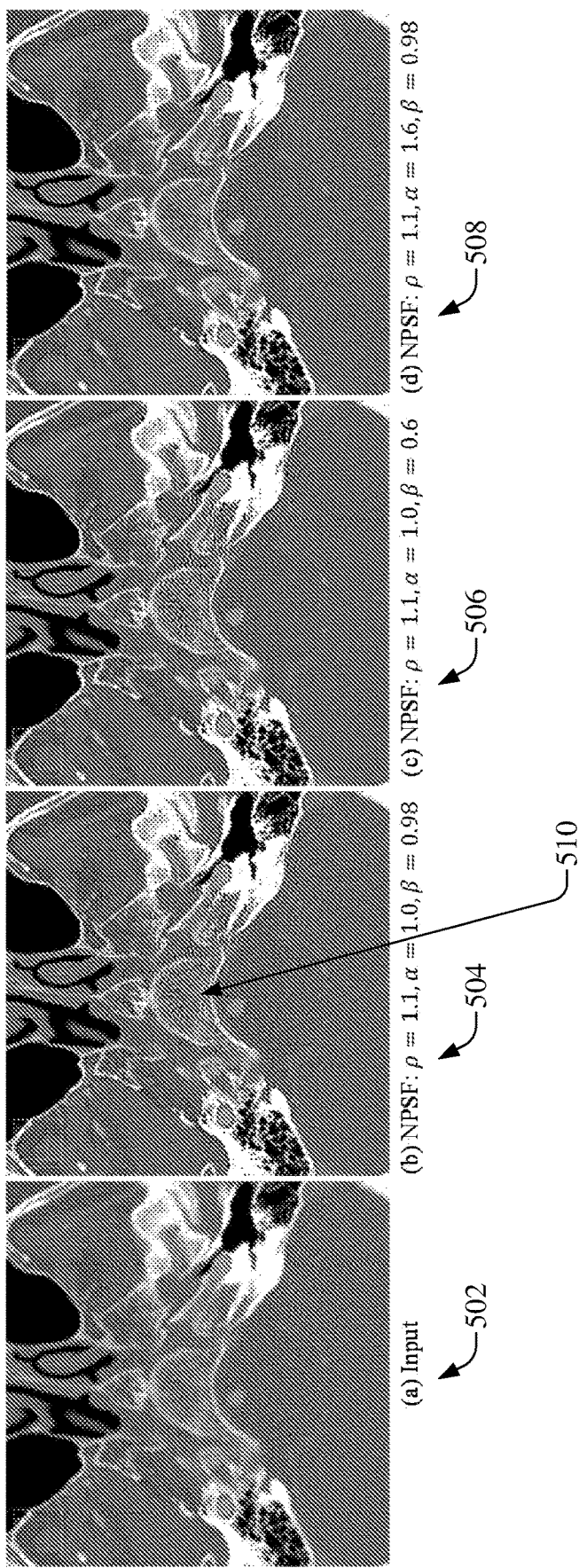
FIG. 5 illustrates effectiveness of parameters $\alpha$ in controlling aliasing, in accordance with various embodiments described herein.
Figure 6:
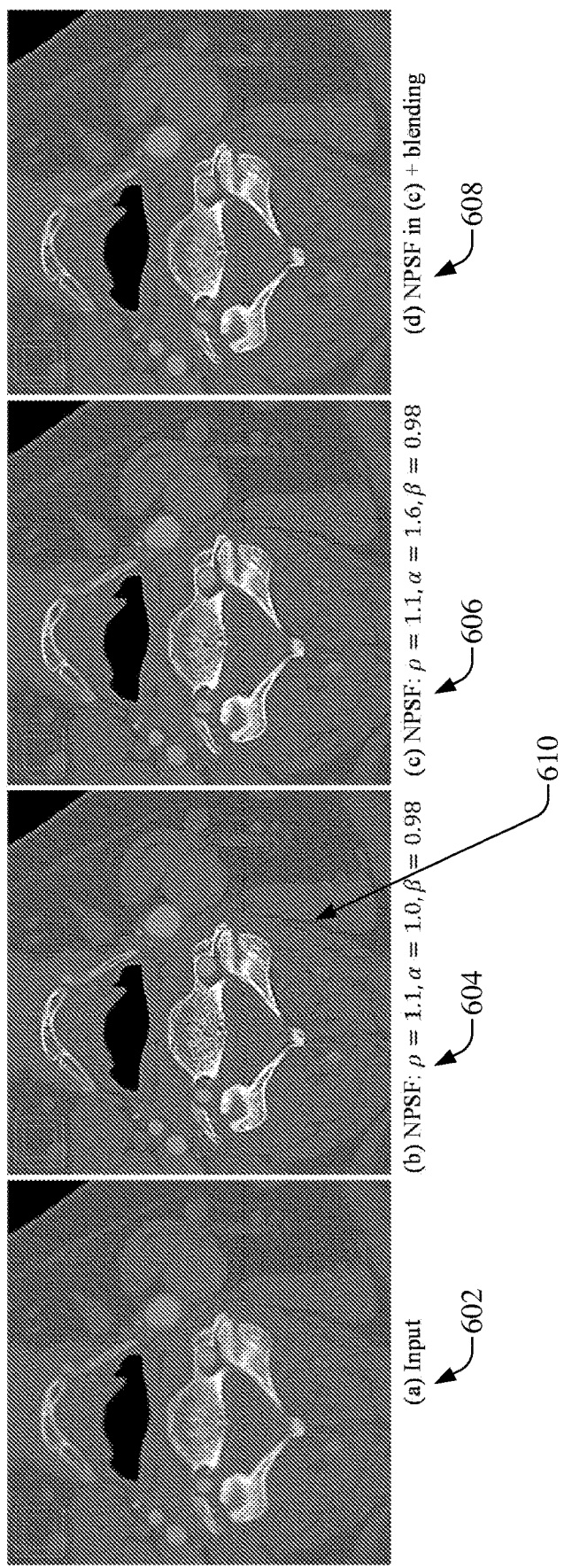
FIG. 6 illustrates the significance of blending to avoid overcorrection of soft tissues, in accordance with various embodiments described herein.
Figure 7:
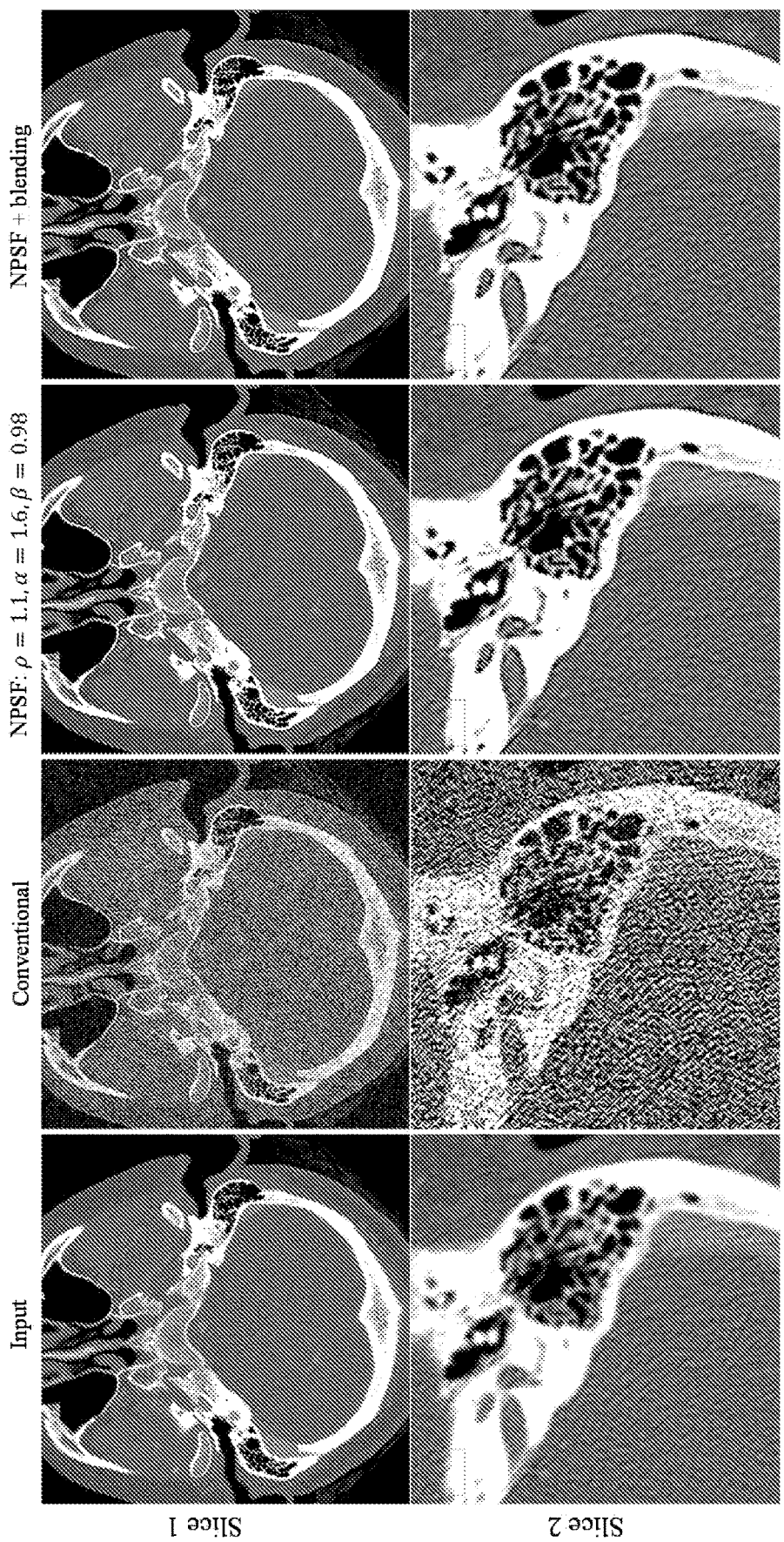
FIG. 7 illustrates resolution recovered results in accordance with various embodiments described herein.

FIG. 5 illustrates the effectiveness of α (e.g., the first adjustable parameter) in controlling aliasing artifacts (e.g., display window [−650, 1350] HU). In FIG. 5, image 502 can comprise a low-resolution input image with aliasing artifacts (e.g., area 510 in image 504) and image 504 can comprise a sharpened image with β set to 0.98 and α set to 1.0 which improves detail, but also increases the aliasing artifacts. As can be appreciated in image 506, reducing β (e.g., to 0.6) can reduce the noise level, however, aliasing artifacts remain unaffected. Image 508 demonstrates that increasing α (e.g., to 1.6) can significantly reduce the aliasing artifacts. FIG. 6 demonstrates the significance of blending to avoid overcorrection of soft tissues (e.g., display window [−650, 1350] HU). In FIG. 6, image 602 can comprise a low-resolution input image. The dark soft tissue boundaries in image 604 and image 606 (e.g., area 610) demonstrate that setting β as $\beta_{NPSF}$ or higher α does not assist with overcorrection. In this regard, image 608 demonstrates that blending herein avoids the overcorrection of soft tissues with minimal compromise with respect to the resolution in high-density areas. FIG. 7 demonstrates the results of utilization of one of more embodiments herein (e.g., via system 102) to recover bone detail without adding artifacts or noise as opposed to conventional methods which significantly increase noise and artifacts when sharpening.

Various embodiments herein can employ artificial-intelligence or machine learning systems and techniques to facilitate learning user behavior, context-based scenarios, preferences, etc. in order to facilitate taking automated action with high degrees of confidence. Utility-based analysis can be utilized to factor benefit of taking an action against cost of taking an incorrect action. Probabilistic or statistical-based analyses can be employed in connection with the foregoing and/or the following.

It is noted that systems and/or associated controllers, servers, or machine learning components herein can comprise artificial intelligence component(s) which can employ an artificial intelligence (AI) model, a machine learning (ML) model, and/or a deep learning (DL) model that can learn to perform the above or below described functions (e.g., via training using historical training data and/or feedback data).

In some embodiments, system 102 can comprise an AI, ML, and/or DL model that can be trained (e.g., via supervised and/or unsupervised techniques) to perform the above or below-described functions using historical training data comprising various context conditions that correspond to various augmented network optimization operations. In this example, such an AI, ML, and/or DL model can further learn (e.g., via supervised and/or unsupervised techniques) to perform the above or below-described functions using training data comprising feedback data, where such feedback data can be collected and/or stored (e.g., in memory) by the system 102. In this example, such feedback data can comprise the various instructions described above/below that can be input, for instance, to a system herein, over time in response to observed/stored context-based information.

AI/ML/DL components herein can initiate an operation(s) associated with a defined level of confidence determined using information (e.g., feedback data). For example, based on learning to perform such functions described above using feedback data, performance information, and/or past performance information herein, a system 102 herein can initiate an operation associated with determining various thresholds herein (e.g., a motion pattern thresholds, input pattern thresholds, similarity thresholds, authentication signal thresholds, audio frequency thresholds, or other suitable thresholds).

In an embodiment, the system 102 can perform a utility-based analysis that factors cost of initiating the above-described operations versus benefit. In this embodiment, the system 102 can use one or more additional context conditions to determine various thresholds herein.

To facilitate the above-described functions, a system 102 herein can perform classifications, correlations, inferences, and/or expressions associated with principles of artificial intelligence. For instance, the system 102 can employ an automatic classification system and/or an automatic classification. In one example, the system 102 can employ a probabilistic and/or statistical-based analysis (e.g., factoring into the analysis utilities and costs) to learn and/or generate inferences. The system 102 can employ any suitable machine-learning based techniques, statistical-based techniques and/or probabilistic-based techniques. For example, the system 102 can employ expert systems, fuzzy logic, support vector machines (SVMs), Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, and/or the like. In another example, the system 102 can perform a set of machine-learning computations. For instance, the system 102 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations.

Figure 8:
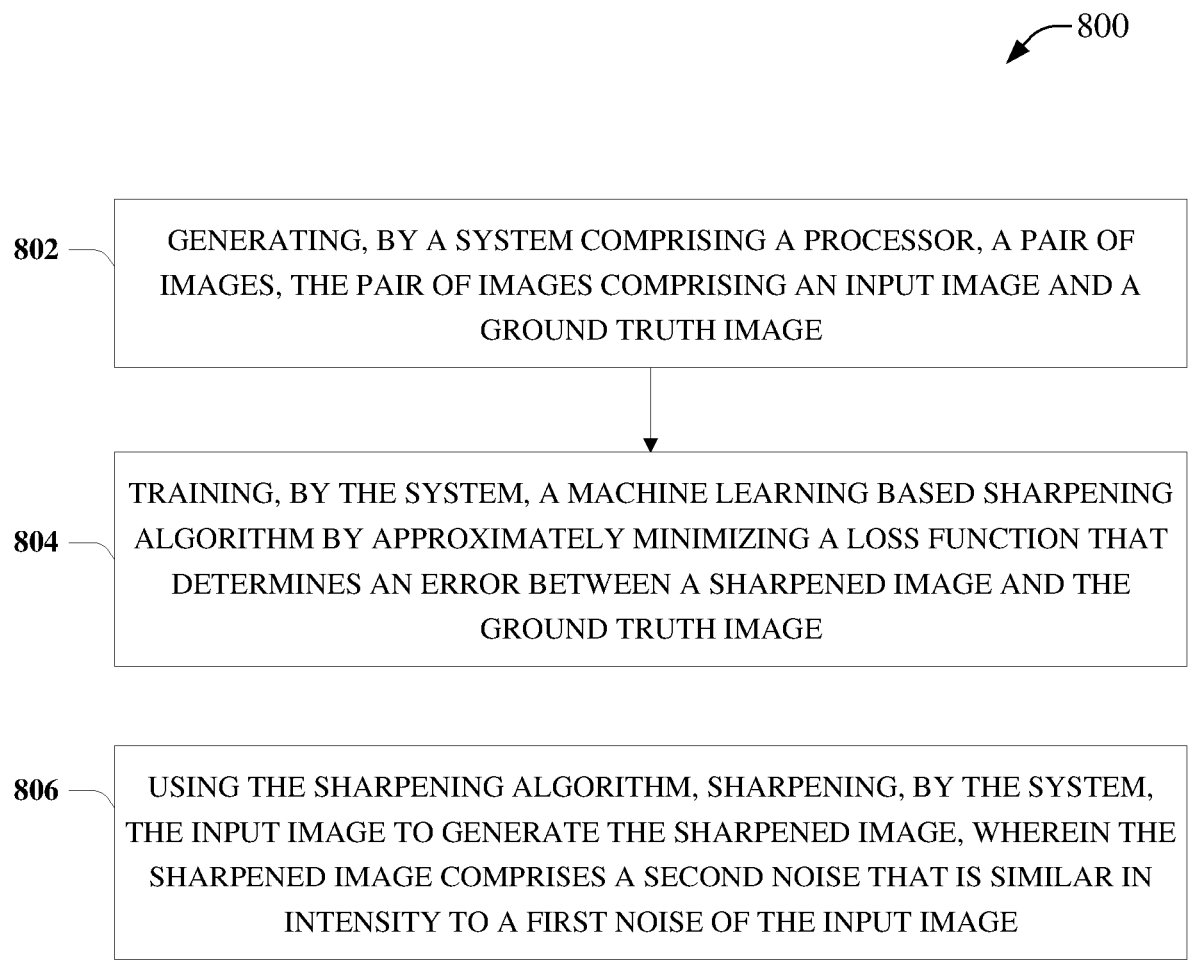
FIG. 8 is a block flow diagram for a process associated with image sharpening in accordance with one or more embodiments described herein.

FIG. 8 illustrates a block flow diagram for a process 800 associated with image sharpening in accordance with one or more embodiments described herein. At 802, the process 800 can comprise generating, by a system comprising a processor (e.g., via the pair generation component 110), a pair of images (e.g., image pair 116), the pair of images (e.g., image pair 116) comprising an input image (e.g., input image 118) and α ground truth image (e.g., ground truth image 120). At 804, the process 800 can comprise training, by the system (e.g., via the training component 112), a machine learning based sharpening algorithm by approximately minimizing a loss function that determines an error between a sharpened image (e.g., sharpened image 122) and the ground truth image (e.g., ground truth image 120). At 806, the process 800 can comprise, using the sharpening algorithm, sharpening, by the system (e.g., via the sharpening component 114), the input image (e.g., input image 118) to generate the sharpened image (e.g., sharpened image 122), wherein the sharpened image (e.g., sharpened image 122) comprises a second noise that is similar in intensity to a first noise of the input image (e.g., input image 118).

Figure 9:
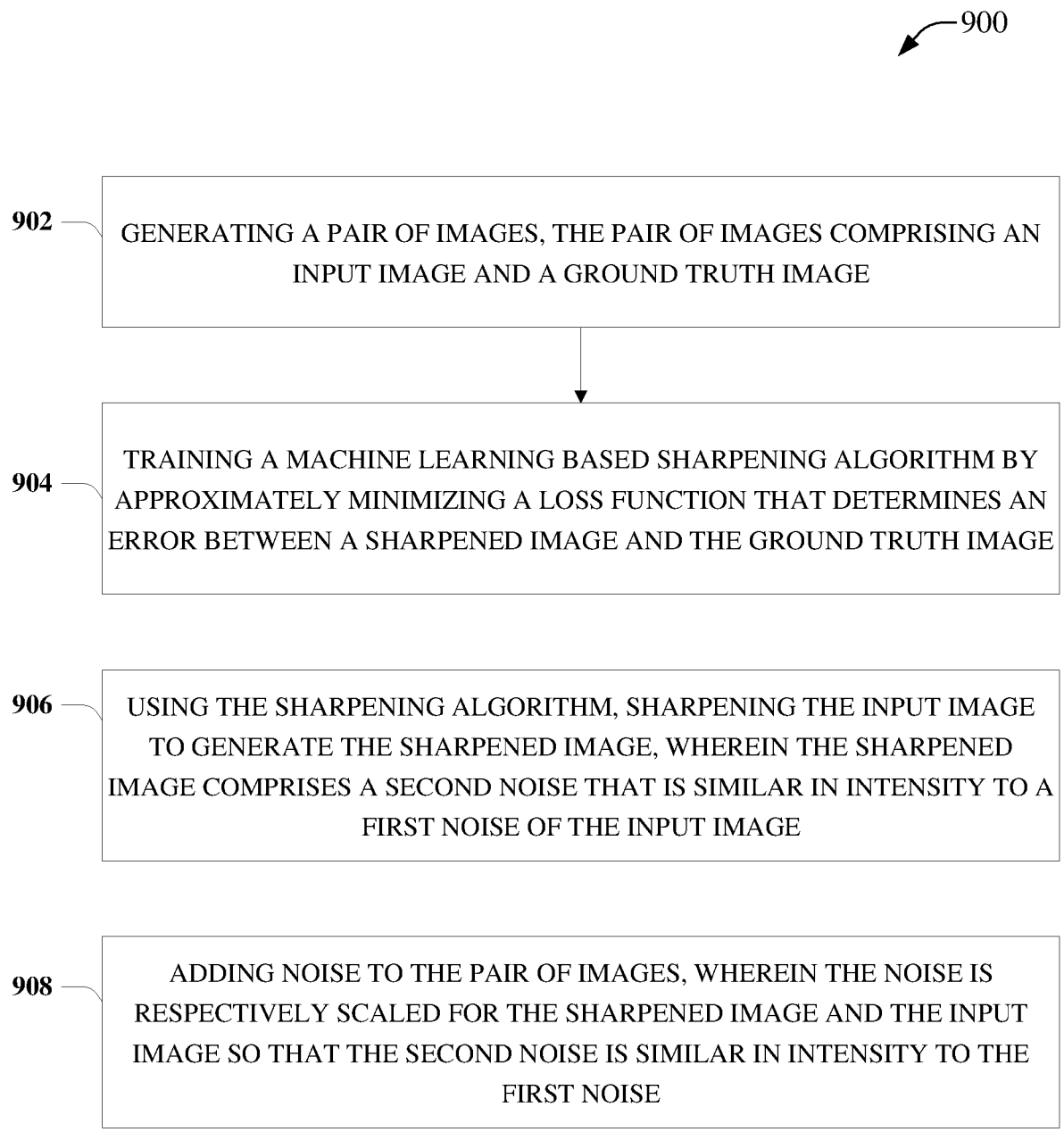
FIG. 9 is a block flow diagram for a process associated with image sharpening in accordance with one or more embodiments described herein.

FIG. 9 illustrates a block flow diagram for a process 900 associated with image sharpening in accordance with one or more embodiments described herein. At 902, the process 900 can comprise generating (e.g., via the pair generation component 110) a pair of images (e.g., image pair 116), the pair of images (e.g., image pair 116) comprising an input image (e.g., input image 118) and a ground truth image (e.g., ground truth image 120). At 904, the process 900 can comprise training (e.g., via the training component 112) a machine learning based sharpening algorithm by approximately minimizing a loss function that determines an error between a sharpened image (e.g., sharpened image 122) and the ground truth image (e.g., ground truth image 120). At 906, the process 900 can comprise, using the sharpening algorithm, sharpening (e.g., via the sharpening component 114) the input image (e.g., input image 118) to generate the sharpened image (e.g., sharpened image 122), wherein the sharpened image (e.g., sharpened image 122) comprises a second noise that is similar in intensity to a first noise of the input image. At 908, the process 900 can comprise adding (e.g., via the noise addition component 124) noise (e.g., noise sample 128) to the pair of images (e.g., image pair 116), wherein the noise is respectively scaled for the sharpened image (e.g., sharpened image 122) and the input image (e.g., input image 118) so that the second noise is similar in intensity to the first noise.

Figure 10:
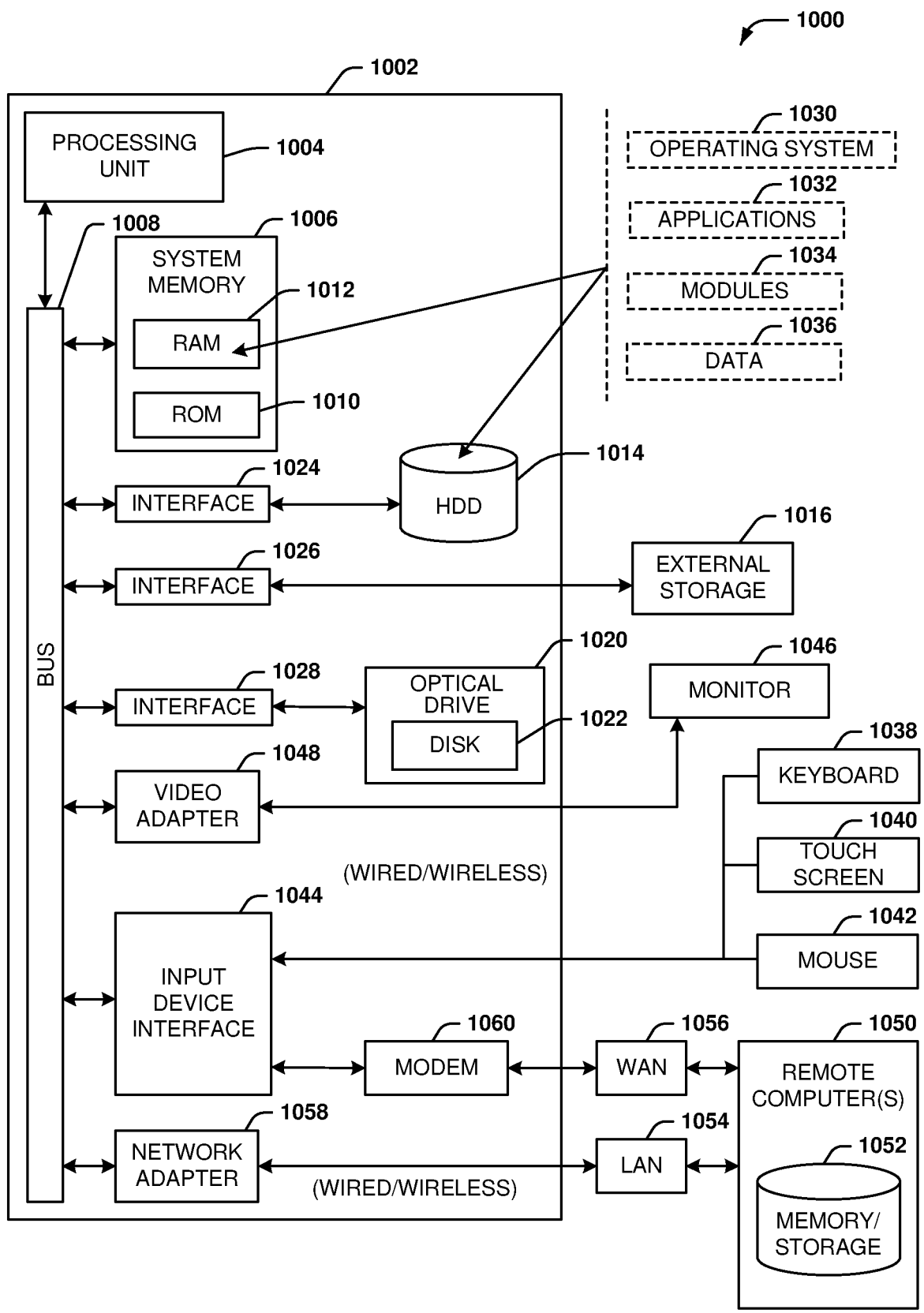
FIG. 10 is an example, non-limiting computing environment in which one or more embodiments described herein can be implemented.

In order to provide additional context for various embodiments described herein, FIG. 10 and the following discussion are intended to provide a brief, general description of a suitable computing environment 1000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the various methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data, or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory, or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries, or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared, and other wireless media.

With reference again to FIG. 10, the example environment 1000 for implementing various embodiments of the aspects described herein includes a computer 1002, the computer 1002 including a processing unit 1004, a system memory 1006 and α system bus 1008. The system bus 1008 couples system components including, but not limited to, the system memory 1006 to the processing unit 1004. The processing unit 1004 can be any of various commercially available processors. Dual microprocessors and other multi-processor architectures can also be employed as the processing unit 1004.

The system bus 1008 can be any of several types of bus structure that can further interconnect to a memory bus (with or without a memory controller), a peripheral bus, and a local bus using any of a variety of commercially available bus architectures. The system memory 1006 includes ROM 1010 and RAM 1012. A basic input/output system (BIOS)

can be stored in a non-volatile memory such as ROM, erasable programmable read only memory (EPROM), EEPROM, where BIOS contains the basic routines that help transfer information between elements within the computer 1002, such as during startup. The RAM 1012 can also include a high-speed RAM such as static RAM for caching data.

The computer 1002 further includes an internal hard disk drive (HDD) 1014 (e.g., EIDE, SATA), one or more external storage devices 1016 (e.g., a magnetic floppy disk drive (FDD) 1016, a memory stick or flash drive reader, a memory card reader, etc.) and an optical disk drive 1020 (e.g., which can read or write from a CD-ROM disc, a DVD, a BD, etc.). While the internal HDD 1014 is illustrated as located within the computer 1002, the internal HDD 1014 can also be configured for external use in a suitable chassis (not shown). Additionally, while not shown in environment 1000, a solid-state drive (SSD) could be used in addition to, or in place of, an HDD 1014. The HDD 1014, external storage device(s) 1016 and optical disk drive 1020 can be connected to the system bus 1008 by an HDD interface 1024, an external storage interface 1026 and an optical drive interface 1028, respectively. The interface 1024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. The systems and methods described herein can be implemented utilizing various commercially available operating systems or combinations of operating systems.

Computer 1002 can optionally comprise emulation technologies. For example, a hypervisor (not shown) or other intermediary can emulate a hardware environment for operating system 1030, and the emulated hardware can optionally be different from the hardware illustrated in FIG. 10. In such an embodiment, operating system 1030 can comprise one virtual machine (VM) of multiple VMs hosted at computer 1002. Furthermore, operating system 1030 can provide runtime environments, such as the Java runtime environment or the .NET framework, for applications 1032. Runtime environments are consistent execution environments that allow applications 1032 to run on any operating system that includes the runtime environment. Similarly, operating system 1030 can support containers, and applications 1032 can be in the form of containers, which are lightweight, standalone, executable packages of software that include, e.g., code, runtime, system tools, system libraries and settings for an application.

Further, computer 1002 can be enabled with a security module, such as a trusted processing module (TPM). For instance, with a TPM, boot components hash next in time boot components, and wait for a match of results to secured values, before loading a next boot component. This process can take place at any layer in the code execution stack of computer 1002, e.g., applied at the application execution level or at the operating system (OS) kernel level, thereby enabling security at any level of code execution.

A user can enter commands and information into the computer 1002 through one or more wired/wireless input devices, e.g., a keyboard 1038, a touch screen 1040, and α pointing device, such as a mouse 1042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1004 through an input device interface 1044 that can be coupled to the system bus 1008, but can be connected by other interfaces, such as a parallel port, an IEEE 1394 serial port, a game port, a USB port, an IR interface, a BLUETOOTH® interface, etc.

A monitor 1046 or other type of display device can be also connected to the system bus 1008 via an interface, such as a video adapter 1048. In addition to the monitor 1046, a computer typically includes other peripheral output devices (not shown), such as speakers, printers, etc.

The computer 1002 can operate in a networked environment using logical connections via wired and/or wireless communications to one or more remote computers, such as a remote computer(s) 1050. The remote computer(s) 1050 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1052 is illustrated. The logical connections depicted include wired/wireless connectivity to a local area network (LAN) 1054 and/or larger networks, e.g., a wide area network (WAN) 1056. Such LAN and WAN networking environments are commonplace in offices and companies, and facilitate enterprise-wide computer networks, such as intranets, all of which can connect to a global communications network, e.g., the Internet.

When used in a LAN networking environment, the computer 1002 can be connected to the local network 1054 through a wired and/or wireless communication network interface or adapter 1058. The adapter 1058 can facilitate wired or wireless communication to the LAN 1054, which can also include a wireless access point (AP) disposed thereon for communicating with the adapter 1058 in a wireless mode.

When used in a WAN networking environment, the computer 1002 can include a modem 1060 or can be connected to a communications server on the WAN 1056 via other means for establishing communications over the WAN 1056, such as by way of the Internet. The modem 1060, which can be internal or external and a wired or wireless device, can be connected to the system bus 1008 via the input device interface 1044. In a networked environment, program modules depicted relative to the computer 1002 or portions thereof, can be stored in the remote memory/storage device 1052. It will be appreciated that the network connections shown are example and other means of establishing a communications link between the computers can be used.

When used in either a LAN or WAN networking environment, the computer 1002 can access cloud storage systems or other network-based storage systems in addition to, or in place of, external storage devices 1016 as described above. Generally, a connection between the computer 1002 and α cloud storage system can be established over a LAN 1054 or WAN 1056 e.g., by the adapter 1058 or modem 1060, respectively. Upon connecting the computer 1002 to an associated cloud storage system, the external storage interface 1026 can, with the aid of the adapter 1058 and/or modem 1060, manage storage provided by the cloud storage system as it would other types of external storage. For instance, the external storage interface 1026 can be configured to provide access to cloud storage sources as if those sources were physically connected to the computer 1002.

The computer 1002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 11:
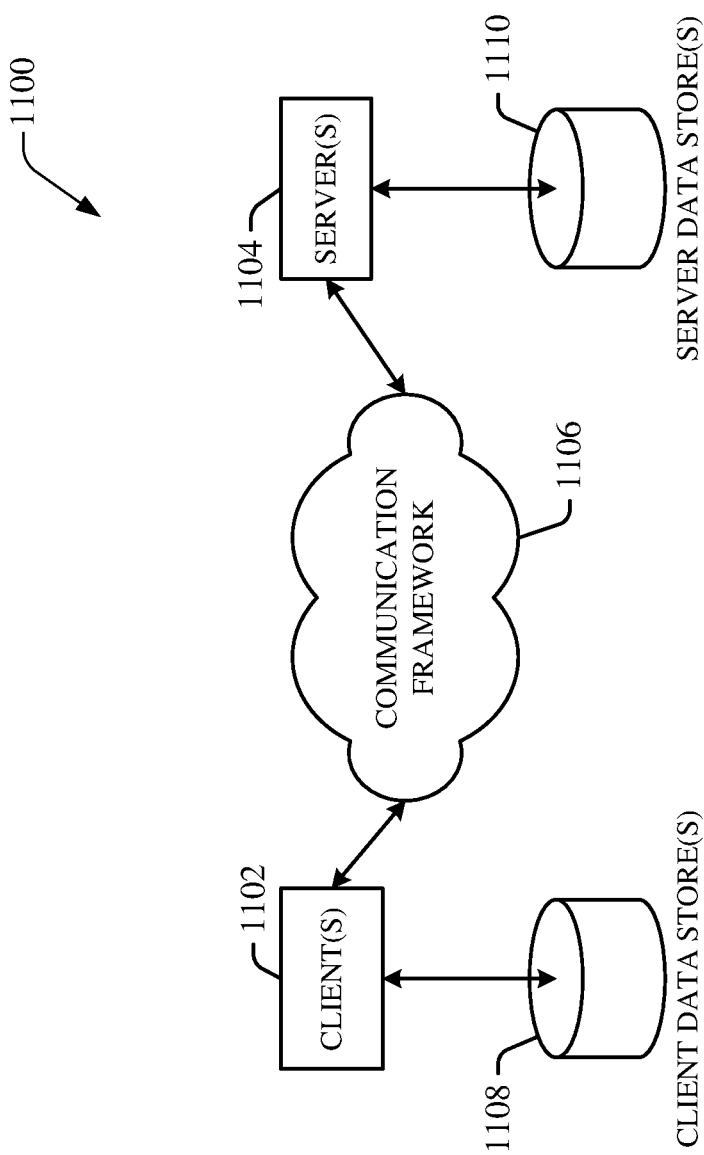
FIG. 11 is an example, non-limiting networking environment in which one or more embodiments described herein can be implemented.

Referring now to FIG. 11, there is illustrated a schematic block diagram of a computing environment 1100 in accordance with this specification. The system 1100 includes one or more client(s) 1102, (e.g., computers, smart phones, tablets, cameras, PDA's). The client(s) 1102 can be hardware and/or software (e.g., threads, processes, computing devices). The client(s) 1102 can house cookie(s) and/or associated contextual information by employing the specification, for example.

The system 1100 also includes one or more server(s) 1104. The server(s) 1104 can also be hardware or hardware in combination with software (e.g., threads, processes, computing devices). The servers 1104 can house threads to perform transformations of media items by employing aspects of this disclosure, for example. One possible communication between a client 1102 and a server 1104 can be in the form of a data packet adapted to be transmitted between two or more computer processes wherein data packets may include coded analyzed headspaces and/or input. The data packet can include a cookie and/or associated contextual information, for example. The system 1100 includes a communication framework 1106 (e.g., a global communication network such as the Internet) that can be employed to facilitate communications between the client(s) 1102 and the server(s) 1104.

Communications can be facilitated via a wired (including optical fiber) and/or wireless technology. The client(s) 1102 are operatively connected to one or more client data store(s) 1108 that can be employed to store information local to the client(s) 1102 (e.g., cookie(s) and/or associated contextual information). Similarly, the server(s) 1104 are operatively connected to one or more server data store(s) 1110 that can be employed to store information local to the servers 1104.

In one exemplary implementation, a client 1102 can transfer an encoded file, (e.g., encoded media item), to server 1104. Server 1104 can store the file, decode the file, or transmit the file to another client 1102. It is noted that a client 1102 can also transfer uncompressed file to a server 1104 and server 1104 can compress the file and/or transform the file in accordance with this disclosure. Likewise, server 1104 can encode information and transmit the information via communication framework 1106 to one or more clients 1102.

The illustrated aspects of the disclosure may also be practiced in distributed computing environments where certain tasks are performed by remote processing devices that are linked through a communications network. In a distributed computing environment, program modules can be located in both local and remote memory storage devices.

The above description includes non-limiting examples of the various embodiments. It is, of course, not possible to describe every conceivable combination of components or methods for purposes of describing the disclosed subject matter, and one skilled in the art may recognize that further combinations and permutations of the various embodiments are possible. The disclosed subject matter is intended to embrace all such alterations, modifications, and variations that fall within the spirit and scope of the appended claims.

With regard to the various functions performed by the above-described components, devices, circuits, systems, etc., the terms (including a reference to a "means") used to describe such components are intended to also include, unless otherwise indicated, any structure(s) which performs the specified function of the described component (e.g., a functional equivalent), even if not structurally equivalent to the disclosed structure. In addition, while a particular feature of the disclosed subject matter may have been disclosed with respect to only one of several implementations, such feature may be combined with one or more other features of the other implementations as may be desired and advantageous for any given or particular application.

The terms "exemplary" and/or "demonstrative" as used herein are intended to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent structures and techniques known to one skilled in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

The term "or" as used herein is intended to mean an inclusive "or" rather than an exclusive "or." For example, the phrase "A or B" is intended to include instances of A, B, and both A and B. Additionally, the articles "a" and "an" as used in this application and the appended claims should generally be construed to mean "one or more" unless either otherwise specified or clear from the context to be directed to a singular form.

The term "set" as employed herein excludes the empty set, i.e., the set with no elements therein. Thus, a "set" in the subject disclosure includes one or more elements or entities. Likewise, the term "group" as utilized herein refers to a collection of one or more entities.

The description of illustrated embodiments of the subject disclosure as provided herein, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as one skilled in the art can recognize. In this regard, while the subject matter has been described herein in connection with various embodiments and corresponding drawings, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A system, comprising:
   a memory that stores computer executable components; and
   a processor that executes at least one of the computer executable components that:
      generates a first set of pairs of training images from a second set of pairs of images, wherein each pair of images of the second set comprises an input image and a noise free ground truth image, wherein the input image is a blurred version of the ground truth image, and wherein the generating comprises, for each pair of images of the second set:
         generating a pair of training images of the first set, comprising:
            generating a training input image by adding a first amount of noise from a noise sample to the input image based on an input image scaling factor, and
            generating a training ground truth image by adding a second amount of noise from the noise sample to the input image based on a ground truth scaling factor, wherein the second amount of noise is scaled to be substantially similar in intensity to the first amount of noise according to a defined threshold;
      trains a machine learning based sharpening algorithm to generate sharpened images, using the first set of pairs of training images, by approximately minimizing a loss function associated with reducing image blur that determines respective errors between the training input images and the training ground truth images of the pairs of training images, and maintains a substantially similar intensity of noise between the training input image and the training ground truth image according to the defined threshold; and
      sharpens, using the sharpening algorithm, a new input image to generate a sharpened image that has reduced image blur as compared to the new input image, wherein the new input image and the sharpened image comprises a substantially similar intensity of noise according to the defined threshold.

2. The system of claim 1, wherein the at least one of the computer executable components further:
   determines, using the sharpening algorithm, an extent of the sharpening of the input image based on an adjustable sharpening parameter.

3. The system of claim 1, wherein the at least one of computer executable components further:
   reduces artifacts in the sharpened image based on a local edge magnitude of the sharpened image.

4. The system of claim 1, wherein the at least one of computer executable components further:
   reduces artifacts in the sharpened image based on Hounsfield Unit values of the sharpened image.

5. The system of claim 1, wherein the input image scaling factor is based on a first adjustable parameter.

6. The system of claim 5, wherein a ground truth scaling factor is based on a second adjustable parameter.

7. The system of claim 1, wherein the noise sample is generated using scans of a water phantom.

8. The system of claim 1, wherein the noise sample is generated by subtracting averaged, high-resolution noise from individual, high-resolution noise.

9. A method, comprising:
   generating, by a system comprising a processor, a first set of pairs of training images from a second set of pairs of images, wherein each pair of images of the second set comprises an input image and a noise free ground truth image, wherein the input image is a blurred version of the ground truth image, and wherein the generating comprises, for each pair of images of the second set:
      generating a pair of training images of the first set, comprising:
         generating a training input image by adding a first amount of noise from a noise sample to the input image based on an input image scaling factor, and
         generating a training ground truth image by adding a second amount of noise from the noise sample to the input image based on a ground truth scaling factor, wherein the second amount of noise is scaled to be substantially similar in intensity to the first amount of noise according to a defined threshold;
   training, by the system, a machine learning based sharpening algorithm to generate sharpened images, using the first set of pairs of training images, by approximately minimizing a loss function associated with reducing image blur that determines respective errors between the training input images and the training ground truth images of the pairs of training images, and maintains a substantially similar intensity of noise between the training input image and the training ground truth image according to the defined threshold; and
   sharpening, by the system, using the sharpening algorithm, a new input image to generate a sharpened image that has reduced image blur as compared to the new input image, wherein the new input image and the sharpened image comprises a substantially similar intensity of noise according to the defined threshold.

10. The method of claim 9, wherein an extent of the sharpening of the input image is determined, using the sharpening algorithm, based on an adjustable sharpening parameter.

11. The method of claim 9, wherein the input image scaling factor is based on a first adjustable parameter, and wherein the ground truth scaling factor is based on a second adjustable parameter.

12. The method of claim 9, wherein the noise sample is generated using scans of a water phantom.

13. The method of claim 9, further comprising:
reducing, by the system, one or more artifacts in the sharpened image based on a local edge magnitude of the sharpened image.

14. The method of claim 9, further comprising:
reducing, by the system, one or more artifacts in the sharpened image based on Hounsfield Unit values of the sharpened image.

15. A non-transitory machine-readable storage medium, comprising executable instructions that, when executed by a processor, facilitate performance of operations, comprising:
generating a first set of pairs of training images from a second set of pairs of images, wherein each pair of images of the second set comprises an input image and a noise free ground truth image, wherein the input image is a blurred version of the ground truth image, and wherein the generating comprises, for each pair of images of the second set:
generating a pair of training images of the first set, comprising:
generating a training input image by adding a first amount of noise from a noise sample to the input image based on an input image scaling factor, and
generating a training ground truth image by adding a second amount of noise from the noise sample to the input image based on a ground truth scaling factor, wherein the second amount of noise is scaled to be substantially similar in intensity to the first amount of noise according to a defined threshold;
training a machine learning based sharpening algorithm to generate sharpened images, using the first set of pairs of training images, by approximately minimizing a loss function associated with reducing image blur that determines respective errors between the training input images and the training ground truth images of the pairs of training images, and maintains a substantially similar intensity of noise between the training input image and the training ground truth image according to the defined threshold; and
using the sharpening algorithm, a new input image to generate a sharpened image that has reduced image blur as compared to the new input image, wherein the new input image and the sharpened image comprises a substantially similar intensity of noise according to the defined threshold.

16. The non-transitory machine-readable storage medium of claim 15, wherein the input image scaling is based on a first adjustable parameter, and wherein the ground truth scaling factor is based on a second adjustable parameter.

17. The non-transitory machine-readable storage medium of claim 15, wherein the noise sample is generated using scans of a water phantom.

18. The non-transitory machine-readable storage medium of claim 15, wherein the noise sample is generated by subtracting averaged, high-resolution noise from individual, high-resolution noise.

19. The non-transitory machine-readable storage medium of claim 15, wherein the operations further comprise:
reducing one or more artifacts in the sharpened image based on a local edge magnitude of the sharpened image.

20. The non-transitory machine-readable storage medium of claim 15, wherein the operations further comprise:
reducing one or more artifacts in the sharpened image based on Hounsfield Unit values of the sharpened image.

* * * * *